(12) United States Patent
Vicidomini et al.

(10) Patent No.: US 9,772,285 B2
(45) Date of Patent: Sep. 26, 2017

(54) STIMULATED EMISSION-DEPLETION (STED) MICROSCOPY BASED ON TIME GATING OF EXCITATION BEAM AND SYNCHRONOUS DETECTION OF FLUORESCENCE EMISSION

(71) Applicant: FONDAZIONE ISTITUTO ITALIANO DI TECNOLOGIA, Genoa (IT)

(72) Inventors: Giuseppe Vicidomini, Genoa (IT); Benjamin Harke, Gottingen (DE); Alberto Diaspro, Genoa (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 0 days.

(21) Appl. No.: 14/911,518

(22) PCT Filed: Aug. 12, 2014

(86) PCT No.: PCT/IB2014/063872
§ 371 (c)(1),
(2) Date: Feb. 11, 2016

(87) PCT Pub. No.: WO2015/022635
PCT Pub. Date: Feb. 19, 2015

(65) Prior Publication Data
US 2016/0187259 A1  Jun. 30, 2016

(30) Foreign Application Priority Data
Aug. 13, 2013  (IT) .............................. TO2013A0692

(51) Int. Cl.
G01N 21/64 (2006.01)

(52) U.S. Cl.
CPC ..... *G01N 21/6458* (2013.01); *G01N 21/6428* (2013.01); *G01N 2021/6439* (2013.01)

(58) Field of Classification Search
CPC ........... G01N 21/6458; G01N 21/6428; G01N 2021/6439
See application file for complete search history.

(56) References Cited

U.S. PATENT DOCUMENTS

| 9,482,612 B2* | 11/2016 | Heidmann | ............. G01N 21/63 |
| 2010/0176307 A1* | 7/2010 | Hell | ..................... G01N 21/636 250/459.1 |
| 2013/0256564 A1* | 10/2013 | Hell | ..................... G01N 21/636 250/459.1 |

OTHER PUBLICATIONS

Emiliano Ronzitti et al. "Frequency dependent detection in a STED microscope using modulated excitation light" Jan. 14, 2013 / vol. 21, No. 1 / Optics Express 210.

(Continued)

*Primary Examiner* — Christine Sung
(74) *Attorney, Agent, or Firm* — Arent Fox LLP

(57) ABSTRACT

Method of optical microscopy by scanning a sample containing an excitable species, the method comprising:
directing a first and a second light beam onto respective, partially overlapped areas of the sample, wherein the first light beam is provided for exciting members of the excitable species, and the second light beam is provided for reducing the number of excited members;
detecting an optical signal coming from the sample, comprising a main component and a spurious component, during consecutive first and second time gates, the first time gate being provided for detecting the optical signal for a time interval during which the main component and the spurious component are both present, and the second time gate being provided for detecting the optical signal for a time interval during which the main component tends to or is zero;

(Continued)

processing the detected optical signal to separate its main component.

6 Claims, 2 Drawing Sheets

(56) References Cited

OTHER PUBLICATIONS

Xiang Hao et al: "Optical super-resolution by subraction of time-gated images", Optics Letters, Optical Society of America, US, vol. 38, No. 6, Mar. 15, 2013 (Mar. 15, 2013), pp. 1001-1003, XP001580713, ISSN: 0146-9592, DOI: http://dx.doi.org/10.1364/01.38.001001.

Giuseppe Vicidomini et al: "Sharper low-power STED nanoscopy by time gating", Nature Methods, vol. 8, No. 7, Jul. 2011 (Jul. 2011) pp. 571-573, XP056115226, ISSN: 1548-7091, DOI: 10.1038/nmeth.1624.

Giuseppe Vicidomini et al: "STED with wavelengths closer to the emission maximum", Optics Express, vol. 20, No. 5, Feb. 27, 2012 (Feb. 27, 2012), pp. 5225-5236, XP055115467, DOI: 10.1364/0E.20.005225.

Giuseppe Vicidomini et al: "STED Nanoscopy with Time-Gated Detection: Theoretical and Experimental Aspects", PLoS One, vol. 8, No. 1, Jan. 18, 2013 (Jan. 18, 2013), pp. e54421-1-12, XP055115463, DOI: 10.1371/journal.pone.054421.

Giuseppe Vicidomini et al: "Gated CW-STED microscopy: A versatile tool for bloiogical nanometer scale investigation"; Jun. 29, 2013 Methods www.elsevier.com/locate/ymeth.

International Search Report dated Oct. 16, 2014.

Michael Lesoine et al. "Supercontinuum Stimulated Emission Depletion Fluorescence Lifetime Imaging", The Journal of Physical Chemistry B 2012, 116, 7821-7826.

* cited by examiner

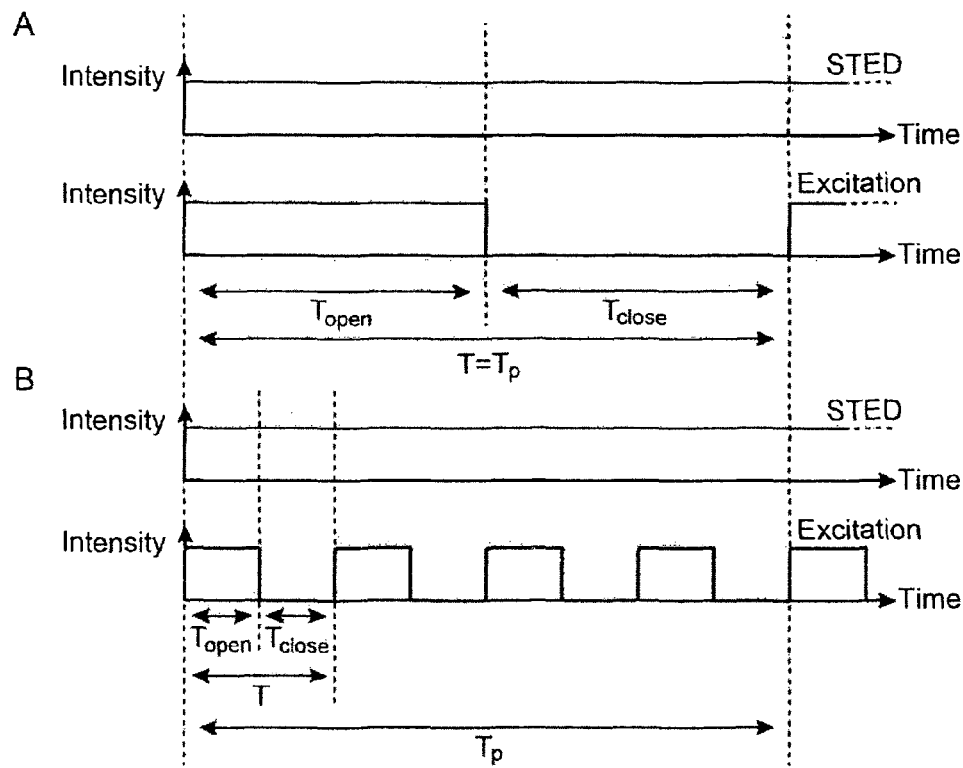
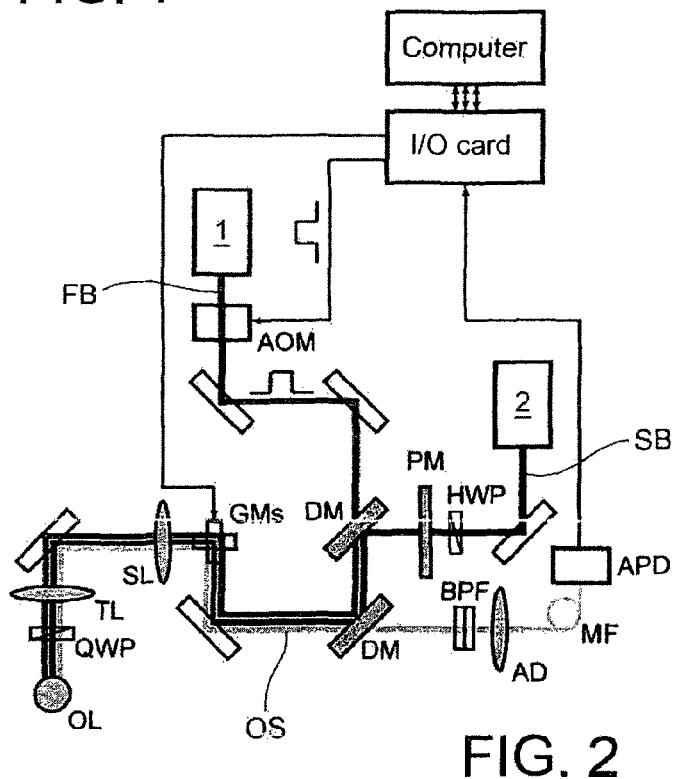
FIG. 1
FIG. 2

STIMULATED EMISSION-DEPLETION (STED) MICROSCOPY BASED ON TIME GATING OF EXCITATION BEAM AND SYNCHRONOUS DETECTION OF FLUORESCENCE EMISSION

CROSS-REFERENCE TO RELATED APPLICATIONS

This application is a National Stage entry of International Application No. PCT/162014/063872 filed on Aug. 12, 2014, which claims priority to Italian Patent Application No. TO2013A000692 filed on Aug. 13, 2013. The disclosures of the prior applications are hereby incorporated in their entirety by reference.

FIELD OF TECHNOLOGY

The present invention relates to imaging methods, and more specifically to high-speed super-resolution microscopy methods capable of resolving details below the Abbe diffraction limit.

BACKGROUND

Among the methods developed up to the present time, stimulated emission depletion (STED) microscopy allows the imaging of the structures of a sample, which are marked with fluorescent probes, with a spatial resolution below the diffraction limit.

In a STED microscope, the excitation beam is spatially overlapped on a second de-excitation beam (also called a STED beam) which can de-excite, by stimulated emission, the fluorescent markers previously excited by the excitation beam. Since the STED beam has at least one zero intensity point (a diffused configuration uses a STED beam with a doughnut section having a zero intensity point at the centre), only the fluorescent markers in the proximity of the zero intensity points can actually emit fluorescence (that is to say, emit spontaneously) when they return to the ground state.

If the intensity of the de-excitation beam is increased, the probability of de-exciting the fluorescent species by stimulated emission increases, and the volume from which the fluorescent species emit decreases, reaching dimensions below the diffraction limit. When the two co-aligned beams are moved and the spontaneously emitted fluorescent light is recorded, the structures of interest marked with the fluorescent species are detected with a spatial resolution above the diffraction limit.

It is important to note that the probability of de-exciting a fluorescent species by stimulated emission depends not only on the intensity of the STED beam but also on the cross section of the stimulated emission process of the fluorescent probe at the wavelength of the STED beam: as the stimulated emission cross section increases, the probability of de-exciting a fluorescent species also increases. Therefore an increase in the stimulated emission cross section is immediately manifested in a reduction of the intensity of the STED beam required to achieve a given spatial resolution, thus reducing potential photodamage effects on the sample.

In STED microscopy, the wavelength of the STED beam is normally located near the red end of the emission peak of the fluorescent species. Shifting the wavelength of the STED beam nearer to the emission peak of the fluorescent species favourably increases the stimulated emission cross section. However, owing to the non-negligible overlap between the emission and excitation spectra, this shift also increases the probability of exciting, directly with the STED beam, the fluorescent species that have remained in the ground state, thereby causing undesirable background fluorescence. Although the fluorescent volume scanned by the excitation beam decreases, potentially improving the spatial resolution as a result, the fluorescent background generated by the STED beam increases the total effective fluorescent volume, thus seriously compromising the image contrast.

Fortunately, this undesired fluorescence background does not distort the spatial frequency content of the image, and in particular it does not alter the effective resolution of the image. In fact, the raw image consists of a super-resolved standard image (below the diffraction limit) generated by the excitation beam, plus a background image generated by the STED beam. Therefore, given a sufficient signal to noise ratio and reliable separate recording of the background image, the super-resolved background image can be retrieved simply by subtracting the recorded background image from the raw image.

It should be noted that, for a given STED wavelength, the possibility of subtracting the undesired background signal (generated by the STED beam) increases the choice of possible fluorescent species that can be used for imaging below the diffraction limit. As mentioned above, given a certain wavelength of the STED beam, it is only the fluorescent species with negligible excitation at the wavelength of the STED beam, and therefore a negligible background, that can conventionally be used successfully for STED imaging. Therefore the provision of a method for removing this background enables the spectral constraints to be relaxed for the fluorescent species, making this method highly important for multicolour imaging (a plurality of species with different spectral properties, each of which marks a different structure within the sample).

In view of the above, the present invention relates, in particular, to a method of optical microscopy by scanning a sample containing an excitable species, said method comprising, for each predetermined scanning segment:

directing a first light beam having a first main wavelength $\lambda_1$, and a second light beam having a second main wavelength $\lambda_2$, on to respective, partially overlapped areas of said sample, wherein said first light beam is provided for exciting, in single- or multi-photon excitation mode, members of the excitable species to an excited state, and said second light beam is provided for reducing the number of excited members in said excited state; and detecting an optical signal coming from the sample, said optical signal comprising a main component emitted by the members excited by said first light beam, and a spurious component emitted by other members of said excitable species undesirably excited by said second light beam, wherein said optical signal is detected during consecutive first and second time gates having respective durations $T_{open}$ and $T_{close}$ and defining a period $T=T_{open}+T_{close}$, said first time gate being provided for detecting the optical signal for a time interval during which the main component and the spurious component are both present, and said second time gate being provided for detecting the optical signal for a time interval during which the main component tends to or is zero while the spurious component remains present;

said method further comprising:
processing the optical signal detected during said second time gate for extracting an estimate of said spurious component; and subtracting said estimate of the spurious component from the optical signal detected during said first time gate.

A method of this kind, described in Vicidomini G et al. (2012), "STED with wavelengths closer to the emission maximum", Opt. Express 20(5):5225-5236, uses the natural interruption of each pulsed laser to define the aforesaid time gates (the "open" and "close" phases). In particular, the time interval between two excitation pulses is divided into two time gates of equal length. The STED beam must operate in continuous wave (CW) mode or with a frequency twice as great as the frequency of the excitation pulses. Furthermore, the frequency of the excitation beam must be accurately chosen on the basis of the average lifetime τ of the excited state of the fluorescent species; in particular, the pulse interval must be sufficiently long to provide effective "open" and "close" phases (most of the fluorescent probes excited in a given phase must be de-excited during the same phase), but a longer pulse interval reduces the useful working cycle of the fluorescent species and only increases the noise. In the context of this scenario, the frequency of the excitation pulses must therefore vary according to the average lifetime of the fluorescent species, making the aforesaid method complicated and inflexible.

Moreover, since the average lifetime τ of the excited state of the fluorescent species is a few nanoseconds in most cases, in the aforementioned known method the "open" and "close" cycle must be completed in a few tens of nanoseconds. However, many detectors have a dead time (that is to say, the time after the recording of a photon during which the detector cannot record another photon) of the order of tens of nanoseconds. Therefore, when a photon is captured during the "open" phase with any probability, a potential photon reaching the detector in the subsequent "close" phase is not recorded, and therefore the background to be subtracted is under-estimated. The total dead time of the detection system increases further if a time-correlated single photon counting (TCSPC) card is used. Furthermore, the method in question is incompatible with STED microscopy based on a continuous wave excitation beam.

Another known method, described in Ronzitti E et al., (2013) "Frequency dependent detection in a STED microscope using modulated excitation light", Opt. Express 21(1): 210-219, uses a pulse generator to modulate the excitation beam at a frequency f and a lock-in amplifier (synchronized with the pulse generator) to selectively detect the fluorescence signal which follows the same frequency f. Since only the fluorescence signal generated by the excitation beam follows the same frequency, the fluorescence signal generated by the STED beam is eliminated by the filtering. The signal obtained from the lock-in amplifier is subsequently collected from an I/O card to form the final image. The lock-in amplifier detects the difference between the signal during the "open" phase of the modulation and the background during the "close" phase of the modulation. Since the pulse generator and the I/O card which control the scanning are independent, the scanning process and the modulation must be synchronized manually, thus reducing the versatility of the method described above.

Furthermore, the lock-in amplifier assumes that there are only "open" and "close" phases having the same duration, making it impossible to maximize the collection of the desired signal in the case of a weak background. Finally, the lock-in amplifier supplies only the signal filtered from the background; in other words, the "open" and "close" signals cannot be accessed separately, and therefore image post-processing methods cannot be used.

SUMMARY

One object of the present invention is to provide a method of optical microscopy which can at least partially overcome the drawbacks of the aforesaid prior art.

This and other objects are achieved according to the invention by a method of optical microscopy of the type defined above, wherein said first light beam is operating during the first time gate $T_{open}$ and is interrupted during the second time gate $T_{close}$, said time gates and said period T being such that $T_{open} \gg \tau$, $T_{close} \gg \tau$ and $T \gg \tau$, where τ is the average lifetime of said excitation state.

This idea for a solution ensures that the members of the chemical species that are excited in a time interval emit in the same time interval; moreover, the risks associated with dead times of the detection apparatus are considerably reduced. Furthermore, the method according to the present invention eliminates or at least reduces the constraints on the apparatus to be used, and is therefore applicable in all STED microscopy configurations, whether of the pulsed wave or the continuous wave type.

Furthermore, the method according to the present invention makes it possible to use "open" and "close" time gates having different durations, and allows separate access to the data measured during these phases, thus enabling the data processing to be adapted to requirements according to the experimental conditions encountered.

Although the present invention has been devised specifically in the field of STED microscopy, it can, clearly, also be used in other super-resolution microscopy methods, referred to jointly by the acronym RESOLFT (REversible Saturable OpticaL Fluorescence Transitions).

BRIEF DESCRIPTION OF THE FIGURES

Further characteristics and advantages of the method according to the invention will be made clearer by the following detailed description of an embodiment of the invention, given with reference to the attached drawings which are provided purely as non-limiting illustrations, in which:

FIGS. 1A and 1B show timing charts of the waveform of the excitation and STED beams in a method according to the present invention;

FIG. 2 is a schematic representation of a preferred STED microscope set up to use the method according to the present invention.

DETAILED DESCRIPTION

Figure 3:
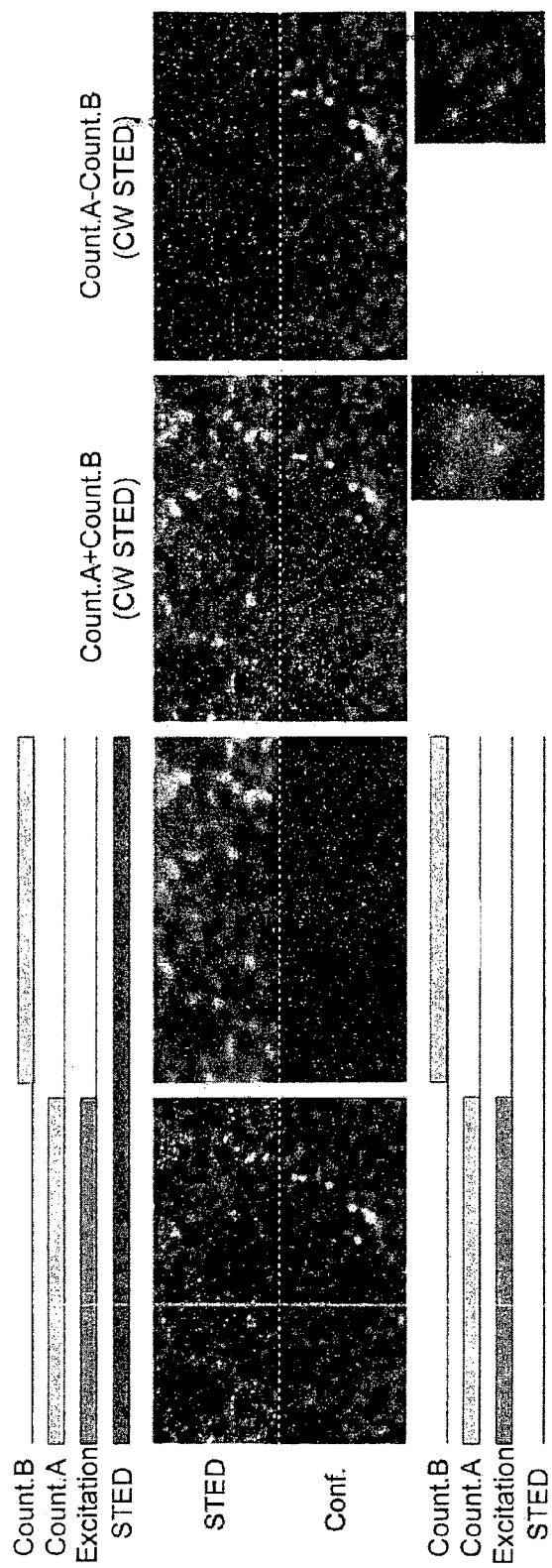
FIG. 3 shows an example of the proposed method used on a calibration sample (40 nm diameter fluorescent balls, considerably below the limit of resolution). The panels show the comparison between the conventional method, also known as the confocal method (bottom panels), that is to say a non-active STED beam, and the super-resolution STED method (top panels). From left to right: (i) Signal recorded in the "open" phase in which the excitation beam is active. (ii) Signal recorded in the "close" phase in which the excitation beam is de-activated, while the STED beam remains active (note that the excitation laser is switched off and on for each pixel). (iii) Sum of the signals recorded in the two phases, to simulate the result that would have been obtained without the differentiated recording of the two phases; in other words, the top panel shows the low-contrast raw STED image. (iv) Subtraction of the signals to retrieve the contrast of the image. The last of the top panels therefore shows the result of the proposed method.

The method of optical microscopy according to the present invention provides, in a conventional way, scanning of a sample containing an excitable species, typically a species that emits fluorescence when it changes from the excited state to the ground state.

For each predetermined scanning segment, the method provides for the direction of a first light beam (typically an excitation beam) having a first main wavelength $\lambda_1$, and a second light beam (typically a de-excitation beam, particularly an STED depletion beam) having a second main wavelength $\lambda_2$, on to respective partially overlapped areas of the sample. The first light beam is provided for exciting, in single- or multi-photon excitation mode, members of the excitable species to an excited state, and said second light beam is provided for reducing the number of excited members that are in the excited state.

In the following description, it is assumed for simplicity that the predetermined scanning segment coincides with a scanning pixel. However, this scanning segment may comprise a plurality of consecutive scanning pixels, in particular a whole scanning line. The invention therefore also applies to the case in which the illumination and detection cycles are associated with a scanning segment longer than one pixel, and in particular equal to a scanning line (see below).

The method therefore provides for the detection of an optical signal received from the sample; this optical signal comprises a main component emitted from the excited members by the first light beam, and a spurious component (background), emitted by other members of the excitable chemical species undesirably excited by the second light beam.

For this purpose, the method according to the present invention makes use of a synchronous detection system to reliably estimate and subsequently subtract the undesired background (of fluorescence) generated by the direct excitation of the fluorescent species with the second light beam (the STED beam).

It is important to note that, in the context of imaging, synchronous detection is performed pixel by pixel (with the advantages discussed below). With reference to FIG. 1, the synchronous detection system requires a periodic interruption of the excitation beam; in other words, the excitation beam is active for a time $T_{open}$ (the "open" time gate or phase) and interrupted for a time $T_{close}$ (the "close" time gate or phase); therefore $f=1/(T_{open}+T_{close})$ and $T=T_{open}+T_{close}$ represent, respectively, the frequency and period of the square wave signal used for the periodic interruption of the excitation beam. The periodic interruption of the excitation beam can be achieved by using the modulation characteristics of the laser source that generates the light beam, or external devices such as acousto-optic modulators (AOM), fast mechanical shutters, electro-optic modulators (EOM) or acousto-optic tunable filters (AOTF).

The optical signal received from the sample is then detected in a synchronous manner with the timing of the excitation beam, during the consecutive "open" and "close" time gates; the first, "open", time gate is provided for detecting the optical signal for a time interval in which the main component and the spurious component of the optical signal are both present, while the second, "close", time gate is provided for detecting the optical signal for a time interval during which the main component tends to or is zero, the spurious component remaining present.

Certain constraints must be respected in the estimation of the background fluorescence:

(i) the dwell time $T_p$ on each scanning pixel must be a multiple of the period T, that is to say $T_p=aT$ where $a\in[1, 2, \ldots, N]$;

(ii) the period T must be much longer than the average lifetime $\tau$ of the excitation state of the excitable chemical species, so that the members of the chemical species that are excited in a time interval (phase) emit in the same time interval. In particular, T must be at least two orders of magnitude greater than $\tau$, in other words such that $(T/\tau) \geq 10^2$. This characteristic can easily be obtained, since normally $T_p$, which may be of substantially the same order of magnitude as T, is three (or more) orders of magnitude greater than $\tau$;

(iii) the duration of the "close" phase must be shorter than or equal to that of the "open" phase, but of the same order of magnitude: $1 \leq (T_{open}/T_{close}) \leq 10$. The shorter the "close" phase is (relative to the "open" phase), the poorer is the estimate of the fluorescent background. A longer "close" phase may be used to maximize the collection of the desired signal for a given time and thereby speed up the acquisition (in other words, reduce the dwell time on the pixel).

The synchronous detection system uses two different counters and a single detector. Both counters use the same detector as the signal source. The detector may be analogue (conventionally, a photomultiplier tube (PMT)) or digital (conventionally, an avalanche photodiode (APD)). In a digital embodiment, based on what is known as "gated photon counting", the first counter counts the APD pulses (photons) during the "open" phase and therefore measures the signal plus the background. The second counter counts the APD pulses (photons) during the "close" phase, and therefore measures only (or practically only) the background. The difference between the counts $c_{open}$ of the "open" phase and the counts $c_{close}$ of the "close" phase (weighted with a factor that allows for the time difference between the two phases) is the retrieved signal $s = c_{open} - (T_{open}/T_{close})c_{close}$. It should be noted that, in the example described herein, the synchronous detection uses subtraction, in other words the fastest and most natural procedure, to retrieve the signal s. However, given the values $c_{open}$ and $c_{close}$, it is possible to devise other, more robust procedures (see below). In conceptual terms, the similar case known as "gated integration" is identical to gated photon counting, except that only the PMT pulses exceeding a certain threshold discrimination level are counted. In the case of multiple cycles, that is to say where $a>1$, the data are simply accumulated before the move is made to the next pixel.

Theoretically, the present invention can be applied to any existing STED microscope, regardless of the type of excitation source and STED source. In the case of pulsed lasers, the frequency of interruption of the excitation beam must be chosen in such a way that "open" and "close" phases are actually created, and therefore it must be chosen with allowance of the pulse interval of the excitation beam; in particular, it must be chosen so as to be much lower than the pulse frequency of the excitation beam.

The pixel by pixel system is helpful for the estimation of a real value for the background, since it minimizes many undesired sources of signal fluctuation, such as photobleaching of the fluorescent chemical species or drifting of the sample. Similarly, the choice of the frequency f for the interruption of the excitation beam is an important parameter for the minimizing of the signal fluctuation source between the "open" and "close" phases. As mentioned above, the choice of this frequency is limited by the average lifetime of the fluorescent chemical species (the upper limit) and the dwell time on the pixel (the lower limit). As a general rule, however, a high frequency (but one such that the period T is greater than τ) avoids differences between the independently measured background (the "close" phase) and the background contribution in the "open" signal (apart from the counting noise). When a high frequency is used, the "open" and "close" phases are measured virtually simultaneously. Therefore the high-frequency interruption of the excitation beam cancels many of the undesired signal fluctuations due to instabilities in the laser output, bleaching, drifting, and other factors.

As usual, the efficiency of the synchronous detection system is fundamentally limited by the signal to noise ratio (SNR). The method according to the invention finds the number of fluorescent photons representing the signal, $N_{des}$, by subtracting the number of fluorescent photons representing the background, $N_{back}$, (collected during the "close" phase) from the total number of fluorescent photons (collected during the "open" phase). The desired fluorescent signal can therefore be retrieved if $N_{des} > \sqrt{(N_{des} + 2N_{back})}$ or, in an equivalent way, if the $SNR = N_{des}/\sqrt{(N_{des} + 2N_{back})}$ of the subtracted signal is >1. It should be noted that this relation takes only the counting noise of the photons into account, on the assumption that all other noise sources are excluded by the high-frequency interruption of the excitation beam (in this respect, synchronous detection is equivalent to any lock-in detection system). However, if the phases are not equal, that is to say if $T_{open}/T_{close} > 1$, the accuracy of the estimation of $N_{back}$ decreases, and therefore the actual SNR may deteriorate further. It is therefore important to use phases of different durations only if there is a weak fluorescent background $N_{back}$ (relative to the desired fluorescence signal $N_{des}$).

Various devices and strategies may be used to implement the method proposed above. The most immediate and versatile implementation uses only one input/output (I/O) card, which supplies all the interface functions required by the method. FIG. 2 shows a possible exemplary embodiment of a STED microscope set up to use the method according to the invention.

A first light source 1, in particular a laser source, supplies a first light beam FB having a main wavelength $\lambda_1$ in the visible range, for example 532 nm. The source 1 may be of a continuous wave type or a pulsed type. The first beam FB is the excitation beam, provided for exciting members of an excitable chemical species contained in a sample for analysis (not shown).

An acousto-optic modulator AOM is provided after the light source 1 in order to modulate the first beam FB with an interruption frequency f. Alternatively, this modulator can be replaced, for example, by an electro-optic modulator (EOM) or an acousto-optic tunable filter (AOTF). In an alternative embodiment, not shown, the light source is itself capable of generating a modulated excitation beam, and the separate modulator can therefore be omitted. In the illustrated example, the modulator AOM uses a square wave modulating signal generated by a computer-controlled I/O card for its operation.

An optical system of the type conventionally used for RESOLFT methods is adapted to direct the excitation beam FB on to a predetermined area of the sample for analysis, and is further equipped to perform a scan of this area and then to shift the focusing area along the surface of the sample. This optical system can comprise, in a conventional way, mirrors, dichroic mirrors DM, galvanometric mirrors GMs, a scanning lens SL, a tube lens TL, a quarter-wave plate QWP, and an objective lens OL.

A second light source 2, in particular a laser source, supplies a second light beam SB, in particular a de-excitation beam, at 642 nm for example. The source 2 may be of a continuous wave type or a pulsed type. The de-excitation beam SB is provided to reduce the number of excited members in said excitation state. In an alternative embodiment, not shown, it is possible to arrange for the excitation beam and the de-excitation beam to be generated by the same source capable of generating different wavelengths.

In the illustrated example, a mirror, a half-wave plate HWP, a phase mask PM, a phase delay plate PP, and the optical system described above are all positioned after the source 2.

This optical system is adapted to additionally focus the de-excitation beam SB on to a predetermined area of the sample for analysis, which partially overlaps the focusing area of the excitation beam FB and which can be moved together with the latter along the surface of the sample.

Typically, the de-excitation beam SB produces a doughnut-shaped spot on the sample, this spot overlapping a peripheral portion of a central spot produced by the excitation beam. The sample then emits an optical signal OS determined by the overlapping of the effects of the excitation beam and the de-excitation beam. Typically, this is a fluorescence signal. As mentioned previously, the emitted optical signal comprises a main component, generated by the interaction of the excitation beam FB with the excitable chemical species contained in the sample, and a spurious component, of greater or lesser intensity, generated by the undesired excitation of the excitable chemical species caused by the de-excitation beam SB.

By means of the aforesaid optical system, the fluorescence signal OS is transmitted, through a bandpass filter BPF, an achromatic doublet AD and a multimode fibre MF, to an avalanche photodiode APD adapted to receive this optical signal and to provide a corresponding electrical detection signal. The photodiode APD may be replaced, for example, with a photomultiplier tube.

The electrical signal supplied by the photodiode is finally received by the computer through the I/O card.

In the configuration described above, the I/O card supplies the square wave signal which periodically interrupts the excitation beam and synchronizes the opening and closing of the two counters (for the "open" and "close" phases respectively). The two counters are provided by the I/O card, and therefore no external devices are required. At the end of each scanning pixel, the I/O card supplies two values which are proportional to the photons collected in the "open" and "close" phases respectively. Additionally, since the scanning process is normally controlled by the same I/O card, the synchronization of the scanning process with the time-gated detection system (counters) is also provided immediately. This is convenient, since the dwell time $T_p$ normally changes according to the application and the sample. Consequently, the frequency f of interruption of the excitation beam and the synchronization of the detection gates must vary in a corresponding manner. All these operations are automatically implemented by the I/O card, since this card acts as the master for the scanning process, the interruption of the excitation beam and the synchronized detection.

Every time that the scanning process moves to a new pixel, the signals counted through the two time gates, that is to say the "open" and "close" signals, are subtracted to generate the retrieved signal s, and the restored images are constructed in real time.

At the same time, it is also possible to obtain the two whole images representing the two phases. This possibility could be very useful if the pixel by pixel subtraction is replaced with more advanced algorithms such as an image deconvolution algorithm. Although the subtraction method is fast and immediate, it is fundamentally limited by the reduction of the SNR, and does not allow for spatial correlations. By producing two images, representing the "open" and "close" phases respectively, it is possible to merge them by an image deconvolution which also allows for the correlation between neighbouring pixels, thus improving the SNR.

The inventors have developed a prototype capable of implementing the invention, by applying a synchronous detection method to an existing CW-STED set-up so as to provide the architecture shown in FIG. 2.

In the CW-STED set-up, the excitation beam was supplied by an continuous-wave optically pumped semiconductor laser (OPSL) emitting at 532 nm, while the STED beam was supplied by a CW fibre laser emitting at 642 nm (MPB Communications, Canada). A vortex phase plate (RPC Photonics, USA) placed on the path of the STED beam generated the phase delay required to form a doughnut-shaped light distribution on the sample. The excitation and STED beams were combined by a dichroic mirror (AHF Analysentechnik, Germany), deflected by two galvanometric scanning mirrors (CTI-Cambridge) and directed towards the objective lens (HCX PL APO 100x/1.40-0.70 Oil, Leica Microsystems) by the same set of scanning and tube lenses as that used in a commercial scanning microscope (Leica TCS SP5, Leica Microsystems). The fluorescence was de-scanned and separated from the reflected excitation and STED beams by means of a dichroic mirror (AHF Analysentechnik) and a bandpass fluorescence filter (AHF Analysentechnik). The filtered fluorescence was focused on a multimode fibre (Thorlabs, Germany) acting as a stenopaeic hole corresponding to a diameter of 1 Airy unit. The output of the fibre was connected to a single-photon avalanche diode (SPAD). The scanning and the data processing of the collected signal were controlled by means of an FPGA card (PCI-7833R, National Instruments, USA) and Imspector software (Abberior Instruments, Germany). To convert the microscope described above into a microscope capable of implementing the invention, an acousto-optic modulator (AA Optoelectronic, France) was introduced into the path of the excitation beam, this modulator periodically interrupting the excitation beam according to a square wave generated by the FPGA card. The FPGA card also controlled the synchronized opening and closing of the two gates which counted the photons of the "open" and "close" phase, respectively.

FIG. 3 shows some images to provide an example of the improvement obtained by using the method according to the invention, relative to a conventional CW-STED architecture. In particular, 40 nm red fluorescent balls were used, characterized by high excitation at the wavelength used for the STED beam.

As mentioned above, the invention also applies to the case in which the illumination and detection cycles are associated with a scanning segment longer than one pixel, and in particular equal to a scanning line. In this case, the cycle(s) of interruption of the excitation beam will take place at the image line level, rather than at the pixel level. That is to say, a line of the image is acquired with both of the beams active, and the same line is then acquired using the STED beam only. At this point, the signals of the two passages of the line are processed (being subtracted, in particular) and the method moves to the next line. Clearly, the process for each line can be repeated for a plurality of times, in the same way as in the case of a plurality of interruptions of the beam on the same pixel (a>1).

The invention claimed is:

1. Method of optical microscopy by scanning a sample containing an excitable species, said method comprising, for each predetermined scanning segment:

directing a first light beam having a first main wavelength $\lambda_1$, and a second light beam having a second main wavelength $\lambda_2$, onto respective, partially overlapped areas of said sample, wherein said first light beam is provided for exciting, in single- or multi-photon excitation mode, members of the excitable species to an excited state, and said second light beam is provided for reducing the number of excited members in said excited state; and detecting an optical signal coming from the sample, said optical signal comprising a main component emitted by the members excited by said first light beam, and a spurious component emitted by other members of said excitable species undesirably excited by said second light beam, wherein said optical signal is detected during consecutive first and second time gates having respective durations $T_{open}$ and $T_{close}$ and defining a period $T=T_{open}+T_{close}$, said first time gate being provided for detecting the optical signal for a time interval during which the main component and the spurious component are both present, and said second time gate being provided for detecting the optical signal for a time interval during which the main component tends to or is zero while the spurious component remains present;

processing the optical signal detected during said second time gate for extracting an estimate of said spurious component; and subtracting said estimate of the spurious component from the optical signal detected during said first time gate;

wherein said first light beam is operating during the first time gate $T_{open}$ and is interrupted during the second time gate $T_{close}$, said time gates and said period T being such that $T_{open} \gg \tau$, $T_{close} \gg \tau$ and $T \gg \tau$, where $\tau$ is the average lifetime of said excitation state, wherein said period T is such that $(T/\tau) \geq 10^2$.

2. Method according to claim 1, wherein for each predetermined scanning segment said optical signal is detected for a dwell time $T_p$ equal to a multiple of said period T, the optical signal being thereby detected for a plurality of cycles of said first and second time gates.

3. Method according to claim 1, wherein the durations $T_{open}$, $T_{close}$ of said first and second time gates are such that $T_{open} \geq T_{close}$.

4. Method of optical microscopy by scanning a sample containing an excitable species, said method comprising, for each predetermined scanning segment:

directing a first light beam having a first main wavelength $\lambda_1$, and a second light beam having a second main wavelength $\lambda_2$, onto respective, partially overlapped areas of said sample, wherein said first light beam is provided for exciting, in single- or multi-photon excitation mode, members of the excitable species to an excited state, and said second light beam is provided for reducing the number of excited members in said excited state; and detecting an optical signal coming from the sample, said optical signal comprising a main component emitted by the members excited by said first light beam, and a spurious component emitted by other members of said excitable species undesirably excited by said second light beam, wherein said optical signal is detected during consecutive first and second time gates having respective durations $T_{open}$ and $T_{close}$ and defining a period $T=T_{open}+T_{close}$, said first time gate being provided for detecting the optical signal for a time interval during which the main component and the spurious component are both present, and said second time gate being provided for detecting the optical signal for a time interval during which the main component tends to or is zero while the spurious component remains present;

processing the optical signal detected during said second time gate for extracting an estimate of said spurious component; and subtracting said estimate of the spurious component from the optical signal detected during said first time gate;

wherein said first light beam is operating during the first time gate $T_{open}$ and is interrupted during the second time gate $T_{close}$, said time gates and said period T being such that $T_{open} \gg \tau$, $T_{close} \gg \tau$ and $T \gg \tau$ where $\tau$ is the average lifetime of said excitation state, wherein the durations $T_{open}$, $T_{close}$ of said first and second time gates are such that $T_{open} \geq T_{close}$.

5. Method according to claim 4, wherein $1 \leq (T_{open}/T_{close}) \leq 10$.

6. Method of optical microscopy by scanning a sample containing an excitable species, said method comprising, for each predetermined scanning segment:

directing a first light beam having a first main wavelength $\lambda_1$, and a second light beam having a second main wavelength $\lambda_2$, onto respective, partially overlapped areas of said sample, wherein said first light beam is provided for exciting, in single- or multi-photon excitation mode, members of the excitable species to an excited state, and said second light beam is provided for reducing the number of excited members in said excited state; and detecting an optical signal coming from the sample, said optical signal comprising a main component emitted by the members excited by said first light beam, and a spurious component emitted by other members of said excitable species undesirably excited by said second light beam, wherein said optical signal is detected during consecutive first and second time gates having respective durations $T_{open}$ and $T_{close}$ and defining a period $T=T_{open}+T_{close}$, said first time gate being provided for detecting the optical signal for a time interval during which the main component and the spurious component are both present, and said second time gate being provided for detecting the optical signal for a time interval during which the main component tends to or is zero while the spurious component remains present;

processing the optical signal detected during said second time gate for extracting an estimate of said spurious component; and subtracting said estimate of the spurious component from the optical signal detected during said first time gate;

wherein said first light beam is operating during the first time gate $T_{open}$ and is interrupted during the second time gate $T_{close}$, said time gates and said period T being such that $T_{open} \gg \tau$, $T_{close} \gg \tau$ and $T \gg \tau$, where $\tau$ is the average lifetime of said excitation state, wherein for each predetermined scanning segment said optical signal is detected for a dwell time $T_p$ equal to a multiple of said period T, the optical signal being thereby detected for a plurality of cycles of said first and second time gates, wherein the durations $T_{open}$, $T_{close}$ of said first and second time gates are such that $T_{open} \geq T_{close}$.

* * * * *